United States Patent
Kupferschmid et al.

(10) Patent No.: US 12,016,532 B2
(45) Date of Patent: Jun. 25, 2024

(54) ENDOSCOPE WITH PIVOTABLE IMAGE CAPTURING DEVICE

(71) Applicant: KARL STORZ SE & Co. KG, Tuttlingen (DE)

(72) Inventors: Markus Kupferschmid, Tuttlingen (DE); Daniel Ulmschneider, Tuttlingen (DE); Andreas Heni, Tuttlingen (DE); Jonas Forster, Tuttlingen (DE)

(73) Assignee: KARL STORZ SE & CO. KG, Tuttlingen (DE)

( * ) Notice: Subject to any disclaimer, the term of this patent is extended or adjusted under 35 U.S.C. 154(b) by 87 days.

(21) Appl. No.: 17/315,796

(22) Filed: May 10, 2021

(65) Prior Publication Data

US 2021/0378496 A1 Dec. 9, 2021

(30) Foreign Application Priority Data

Jun. 9, 2020 (DE) ...................... 10 2020 115 258.2

(51) Int. Cl.
*A61B 1/05* (2006.01)
*A61B 1/00* (2006.01)

(52) U.S. Cl.
CPC ............ *A61B 1/05* (2013.01); *A61B 1/00096* (2013.01); *A61B 1/00183* (2013.01); *A61B 1/00193* (2013.01)

(58) Field of Classification Search
CPC ............ A61B 1/00071; A61B 1/00096; A61B 1/00135; A61B 1/00179; A61B 1/00193;
(Continued)

(56) References Cited

U.S. PATENT DOCUMENTS

| 4,576,147 A | * | 3/1986 | Hashiguchi | ........ | A61B 1/00179 600/920 |
| 2007/0055103 A1 | * | 3/2007 | Hoefig | ............... | A61B 1/00179 600/137 |

(Continued)

FOREIGN PATENT DOCUMENTS

DE 10 2010 028 147 A1 10/2011
DE 10 2012 206 963 A1 10/2012
(Continued)

*Primary Examiner* — Michael J Carey
*Assistant Examiner* — Timothy Tuan Luu
(74) *Attorney, Agent, or Firm* — Eversheds Sutherland (US) LLP

(57) ABSTRACT

The present application relates to an endoscope apparatus including a shaft component with a proximal end and a distal end. The shaft component is arranged in an outer shaft. The endoscopy apparatus includes an image capture device having an objective lens for generating a real image and an image sensor for capturing the image and generating an image signal. The endoscopy apparatus includes a pivot joint device which couples the image capture device to the shaft component in a manner pivotable about two orthogonal axes but rigid in respect of a rotation about the longitudinal axis of the shaft component. The endoscopy apparatus includes a pivot control device to set a pivot position of the image capture device relative to the shaft component which depends on the rotational position of the image capture device and the shaft component relative to the outer shaft.

15 Claims, 4 Drawing Sheets

(58) Field of Classification Search
CPC ... A61B 1/05; G02B 23/2423; G02B 23/2484
See application file for complete search history.

(56) References Cited

U.S. PATENT DOCUMENTS

| | | | |
|---|---|---|---|
| 2013/0182091 A1* | 7/2013 | Kohno | A61B 1/00064 348/76 |
| 2014/0142385 A1* | 5/2014 | Dahmen | A61B 1/0052 600/173 |
| 2014/0249369 A1 | 9/2014 | Hanabusa | |
| 2015/0359420 A1 | 12/2015 | Hatase et al. | |
| 2018/0341101 A1* | 11/2018 | Heni | A61B 1/00193 |
| 2019/0274526 A1 | 9/2019 | Matsumoto et al. | |
| 2020/0129053 A1* | 4/2020 | Levy | G02B 23/2484 |
| 2021/0282628 A1* | 9/2021 | Tortola | A61B 1/0669 |

FOREIGN PATENT DOCUMENTS

| | | | |
|---|---|---|---|
| DE | 10 2017 103 721 A1 | 8/2018 | |
| EP | 3 243 426 A1 | 11/2017 | |
| WO | WO-2010014421 A1 * | 2/2010 | ......... A61B 1/00042 |
| WO | 2018/065241 A1 | 4/2018 | |

* cited by examiner

ENDOSCOPE WITH PIVOTABLE IMAGE CAPTURING DEVICE

TECHNICAL FIELD

The present invention relates to an endoscope or exoscope with a pivotable image capture device.

BACKGROUND OF THE INVENTION

In addition to endoscopes having a viewing direction parallel to the longitudinal axis of the shaft ("straight look"), use is predominantly made of endoscopes whose viewing direction includes an angle with the longitudinal axis of the shaft, said angle often ranging from 30° to 80° ("forward look"). For some applications, endoscopes with an adjustable angle between the viewing direction and longitudinal axis of the shaft are also considered.

US 2007/0055103 A1 has described an endoscope with a variable viewing direction (title; paragraphs [0002], [0017], and [0018]). An optical imaging system ("optical imaging system") 18 with an imaging optical unit ("imaging optics") 22 and a CCD chip 24 is arranged in a rigid distal head ("rigid distal head") 16 of the endoscope 10 (paragraphs [0073] and [0074]). The distal head 16 is connected to a first shaft section ("first shaft portion") 32 in a manner pivotable about a first pivot axis ("first pivot axis") 38, and the first shaft section 32 is connected to a second shaft section 34 in a manner pivotable about a second pivot axis 40 (paragraphs [0079], [0082], and [0083]).

DE 10 2012 206 963 A1 has described an endoscope which comprises a rotatably mounted retainer 5 with a digital camera 4 at or in a retention means 6, the retention means 6 being arranged in radially rotatable fashion such that the axes of rotation of the retention means 6 and of the retainer 5 are arranged perpendicular to one another (paragraph [0008]).

US 2013/0182091 A1 has described an endoscope with an alterable viewing direction (abstract; paragraph [0002]). An imaging unit ("imaging unit") 12 driven by drive rods 22, 23 of two driving force transmission mechanisms is rotatable about two different axes X, Y (paragraphs [0002], [0028], and [0062]; FIGS. 3, 4, 6, 8 and 9).

US 2015/0359420 A1 has described an endoscope 1 with a partly flexible shaft ("insertion section") 11 and an imaging unit ("imaging unit") 36 at the distal end ("tip end portion") of the shaft 11 (paragraph [0036]; FIG. 1). The imaging unit 6a is arranged in pivotable fashion (paragraphs [0079] and [0081]; FIGS. 4 and 5).

EP 3 243 426 A1 has described an endoscope 100 with an elongate shaft ("elongated shaft") 101 and an image sensor arrangement ("image sensor assembly") 202 (title; abstract; paragraphs [0002], [0008], [0019], and [0022]; FIGS. 1, 2 and 5). The image sensor arrangement 202 can be pivoted about a lateral joint axis ("lateral articulation axis") T1 (paragraph [0026]; FIGS. 2, 3, 5, 6, and 7).

WO 2018/065241 A1 has described a stereo video endoscope 2 having an optical system 20 (title; abstract; page 13, line 26 to page 14, line 7, page 14, lines 27 to 29; FIGS. 1 and 2). By rotating a handle 4, it is possible to rotate the viewing direction about the longitudinal axis of the endoscope shaft 6 (page 14, lines 18 to 21). To maintain the horizontal position of the displayed image, a rotary knob 14 is secured when rotating the handle 4; as a result, the image sensors 52L, 52R in the interior of the endoscope shaft 6 do not carry out the rotational movement (page 14, lines 21 to 25, page 16, lines 2 to 13; FIG. 2).

US 2019/0274526 A1 has described a stereo endoscope 1 having an image capture apparatus ("image pick-up apparatus") 30 in a distal end section ("distal end portion") 11 on the distal side of a bendable section ("bending portion") of the shaft ("long insertion portion") 2 (paragraphs [0021], [0023], and [0025]; FIGS. 1 and 2).

The image generated by the endoscope is also rotated relative to the endoscope when there is a rotation of a viewing direction that deviates from the longitudinal axis of the distal end of the shaft on a conical lateral face around the longitudinal axis of the distal end of the shaft. In the case of an analog endoscope, i.e., a purely optical endoscope, with a camera connected to the eyepiece thereof, this can be avoided by a rotation of the camera in the opposite direction or, expressed differently, by securing the camera while rotating the endoscope. In the case of a monocular video endoscope, the image captured by the co-rotating image sensor can be rotated back digitally. However, in the case of a stereo video endoscope, the stereo basis also rotates with the endoscope. This can also be compensated for digitally by virtue of depth information being calculated from the stereo image, i.e., spatial information being obtained, and a stereo image with the desired basis being synthesized therefrom. However, this requires much computational outlay, and artifacts and image interferences have to be accepted in many situations.

SUMMARY OF THE INVENTION

An object of the present invention consists in developing an improved, in particular mechanically robust and miniaturizable, endoscope or exoscope with a movable viewing direction.

This object is achieved by the subject matter of the independent claims.

Further embodiments are defined in the dependent claims.

Embodiments of the present invention are based on the concept of fastening an image capture device to a distal end of a shaft component in pivotable but non-rotatable fashion and of controlling the pivot position of the image capture device by a pivot control device in a manner dependent on the rotational position of an outer shaft.

An endoscope apparatus comprises a shaft component having a proximal end and a distal end for insertion into a cavity, wherein the shaft component is arranged in an outer shaft or provided and embodied for arrangement in an outer shaft, an image capture device having an objective lens for generating a real image and an image sensor for capturing the real image and for generating an image signal which represents the captured real image, wherein the image capture device is arranged at the distal end of the shaft component, a pivot joint device which couples the image capture device to the shaft component in a manner pivotable about two orthogonal axes but rigid in respect of a rotation about the longitudinal axis of the shaft component, and a pivot control device for setting a pivot position of the image capture device relative to the shaft component in a manner dependent on a rotational position of the outer shaft relative to the image capture device and the shaft component.

The endoscope apparatus is provided and embodied, in particular, for use in medical measures, especially in micro-invasive medical measures. Alternatively, the endoscope apparatus can be provided and embodied for non-medical applications.

The outer shaft can be a constituent part of the endoscope apparatus such that the endoscope apparatus represents a complete and usable endoscope which only still needs to be combined with apparatuses outside of the operating field, in particular with a light source, a camera control unit (CCU), image processing, and a monitor. In this case, the outer shaft can be mechanically connected in permanent and not readily separable fashion to the remaining components of the endoscope, in particular to the shaft component. Not readily separable means not without the use of tools that are typically not available in a treatment room or operating theater. Alternatively, the outer shaft may be, e.g., removable for cleaning or repair purposes or replaceable for altering the angle between the viewing direction and shaft axis, and may be separable from the other components of the endoscope apparatus to this end, in particular without the need for tools.

Alternatively, the outer shaft is not a constituent part of the endoscope apparatus. In this case, the endoscope apparatus only forms a complete endoscope together with the outer shaft, said complete endoscope being usable—when supplemented by apparatuses from outside of the operating field, specifically light source, camera control unit, image processing device, monitor, and the like. The endoscope apparatus can be provided for use with an outer shaft which can only be used once and/or for use with an outer shaft which can be repeatedly cleaned, sterilized, and reused. The endoscope apparatus can be provided and embodied for use with different outer shafts, which generate different angles between the viewing direction and the longitudinal axis of the distal end of the shaft.

The image capture device is arranged, in particular, directly proximally to an opening or in an opening at the distal end of the outer shaft or is provided and embodied for an arrangement directly proximally to or in said opening. If the outer shaft has an optically transparent window component which is used, however, in fluid-tight or even hermetically sealed fashion, the image capture device is arranged directly proximally to the window component, in particular.

Pivoting the image capture device and hence the viewing direction in a manner dependent on the rotational position of the outer shaft relative to the image capture device and the shaft component can facilitate particularly intuitive control of the viewing direction. Further, a rotatability of the outer shaft can be combined particularly easily with a replaceability of the outer shaft, which can be advantageous, in turn, when cleaning, repairing, or adapting the endoscope to a certain application.

In the case of an endoscope apparatus as described here, the pivot control device comprises, in particular, a first sliding face in the outer shaft and a second sliding face mechanically rigidly connected to the image capture device, for abutment against the first sliding face in the outer shaft.

Not every part of the first sliding face need abut against the second sliding face at all times and not every part of the second sliding face need abut against the first sliding face at all times. The first sliding face refers to that part of the surface of the outer shaft—in particular the inner surface of the outer shaft—which can abut against the second sliding face in the case of any attainable orientation of the outer shaft relative to the shaft component when the endoscope apparatus is used as intended. The second sliding face refers to that part of the surface rigidly connected to the image capture device which can abut against the first sliding face in the case of any attainable orientation of the outer shaft relative to the shaft component when the endoscope apparatus is used as intended.

In particular, the first sliding face is ring-shaped. In particular, the first sliding face is arranged at the distal end of the outer shaft and oriented proximally. The second sliding face can likewise have a ring-shaped embodiment.

The second sliding face can comprise a plurality of portions, with an optical axis of the objective lens of the image capture device being arranged between the portions in particular. In particular, the second sliding face is formed at a carrier or housing of the image capture device. In particular, the second sliding face is oriented substantially distally.

The design of the sliding faces can define, in interlocking fashion, the relationship between the rotational position of the outer shaft relative to the image capture device and the shaft component on the one hand and the orientation of the image capture device and its viewing direction on the other hand.

In the case of an endoscope apparatus as described here, the first sliding face is arranged at the edge of the inner surface of a window component of the outer shaft in particular.

In the case of an endoscope apparatus as described here, a surface normal of the inner surface of the window component is tilted relative to a longitudinal axis of the distal end of the outer shaft in particular, wherein the first sliding face is a portion of the inner surface of the window component.

In particular, an edge region of the inner surface of the window component is embodied as first sliding face.

If the inner surface of the window component and hence, in particular, the entire window component is tilted in relation to the longitudinal axis of the distal end of the shaft component and of the distal end of the outer shaft, the first sliding face is also tilted in relation to the longitudinal axis. If the second sliding face which is mechanically rigidly connected to the image capture device abuts against the first sliding face, the image capture device, and hence also the viewing direction thereof, has a predetermined orientation relative to the window component independently of the rotational position of the outer shaft. In the case of an orientation of the second sliding face orthogonal to the viewing direction of the image capture device, the viewing direction then is orthogonal to the inner surface of the window component and parallel to the surface normal of the inner surface of the window component.

In the case of an endoscope apparatus as described here, the second sliding face is provided, in particular, at a frame or a carrier or a housing of the image capture device.

By way of example, the image capture device has a cup-shaped carrier, the second sliding face being provided at its substantially distally oriented edge. Alternatively, the image capture device can have a plurality of distally protruding feet or studs, at which a portion of the second sliding face is provided in each case.

In the case of an endoscope apparatus as described here, the objective lens of the image capture device is arranged between two portions of the second sliding face in particular.

The two portions of the second sliding face can be portions of a single contiguous, for example annular, second sliding face. Alternatively, the two portions can be spaced apart from one another and not be connected by other portions of the second sliding face.

An endoscope apparatus as described here further comprises, in particular, a first magnet which is mechanically rigidly connected to the image capture device or mechanically coupled to the latter by way of a force transmission device, and a second magnet which is mechanically rigidly connected to the shaft component or to a proximal region of the endoscope or to the outer shaft, wherein the first magnet and the second magnet are arranged and oriented in such a way that a force between the first magnet and the second magnet exerts a distally directed force on the image capture device.

The distally directed force on the image capture device generated by the interaction of the two magnets can, in particular, press the second sliding face at the image capture device against the first sliding face in the outer shaft and hence facilitate the interlocking definition of the orientation of the image capture device by the contact between the sliding faces.

If the first magnet is directly mechanically rigidly connected to the image capture device, the second magnet is arranged, in particular, directly on the proximal side of the image capture device at the shaft component or at the outer shaft and repels the first magnet distally. Alternatively, the second magnet can be arranged on the distal side of the image capture device or at least on the distal side of the first magnet and attract the first magnet. In this case, the first magnet is provided at a proximal end of the image capture device, in particular.

Alternatively, the first magnet is arranged at a force transmission device, for example at the proximal end of a rod or a pipe. The proximal end of the force transmission device and the first magnet can be arranged at the proximal end of the shaft component or in a handling device at the proximal end of the endoscope apparatus. If the second magnet is arranged on the proximal side of the first magnet, both magnets are oriented in such a way that the second magnet repels the first magnet. If the second magnet is arranged on the distal side of the first magnet, both magnets are oriented in such a way, in particular, that the second magnet attracts the first magnet. The force transmission device transmits the distally oriented force from the interaction of the magnets to the image capture device. The distal end of the force transmission device is connected, in particular in articulated fashion, to the image capture device.

An endoscope apparatus as described here comprises, in particular, a plurality of first magnets which are mechanically rigidly connected to the image capture device or mechanically coupled to the latter by way of force transmission devices, wherein the first magnets and the second magnet are arranged and oriented in such a way that a force between the first magnet and the second magnet exerts a distally directed force on the image capture device.

In particular, the plurality of first magnets have the same orientation and are arranged symmetrically at the image capture device, for example uniformly distributed over the perimeter thereof.

An endoscope apparatus as described here comprises, in particular, a plurality of second magnets which are mechanically rigidly connected to the shaft component or to a proximal region of the endoscope or to the outer shaft, wherein the first magnet or the first magnets and the second magnets are arranged and oriented in such a way that forces between the first magnet or magnets and the second magnet exert distally directed forces on the image capture device.

The second magnets are arranged, particularly in symmetric fashion, at the shaft component or at or in the outer shaft and are oriented in the same way.

An endoscope apparatus as described here further comprises, in particular, a spring or another elastic device with a first end, which is directly mechanically connected to the image capture device or mechanically coupled to the latter by way of a force transmission device, and a second end, which is directly or indirectly mechanically connected to the shaft component or a proximal region of the endoscope, wherein the spring exerts a distally directed force on the image capture device.

The distally directed force on the image capture device generated by the spring causes, in particular, an abutment of the second sliding face of the image capture device against the first sliding face of the outer shaft.

An endoscope apparatus as described here comprises, in particular, a plurality of springs or other elastic devices each with a first end, which is directly mechanically connected to the image capture device or mechanically coupled to the latter by way of a force transmission device, and each with a second end, which is directly or indirectly mechanically connected to the shaft component or a proximal region of the endoscope, wherein the springs exert distally directed forces on the image capture device.

An endoscope apparatus as described here further comprises, in particular, a plurality of first magnets which are mechanically rigidly connected to the image capture device or mechanically coupled to the latter by way of a respective force transmission device, and a magnet arrangement of one or more second magnets which is mechanically rigidly connected to the outer shaft, for generating a guiding magnetic field which generates a force on each of the first magnets in the direction of a position that depends on the rotational position of the image capture device and the shaft component relative to the outer shaft.

The magnet arrangement can cause purely magnetic and, in the ideal case, contactless guidance of the image capture device and can cause a pivoting of the image capture device and the viewing direction in the case of a rotation of the outer shaft.

In the case of an endoscope apparatus as described here, the force transmission device or each of the plurality of force transmission devices comprises, in particular, a rod-like component which is guided so as to movable in its longitudinal direction in or at the shaft component.

The rod-like component is rod-like, in particular in view of its capability of transmitting forces in its longitudinal direction. The rod-like component is, in particular, rod-shaped with a circular, rectangular, or any other cross section.

In the case of an endoscope apparatus as described here, the pivot joint device comprises, in particular, a joint which connects the image capture device to a distal end of the rod-like component.

In the case of an endoscope apparatus as described here, the pivot joint device comprises, in particular, a plurality of joints, wherein each of the plurality of joints connects the image capture device to a distal end of one of the rod-like components.

If the pivot joint device comprises exactly one joint, the latter connects the image capture device to the distal end of the force transmission device, in particular in rotationally rigid fashion, i.e., suppresses a rotation of the image capture device relative to the force transmission device about the longitudinal axis of the force transmission device.

An endoscope apparatus as described here is, in particular, a stereo endoscope apparatus, wherein the image capture device comprises two identical or similar arrangements of respectively one objective lens and one image sensor, which are mechanically rigidly connected to one another.

The image capture device can comprise three or more identical or similar arrangements of respectively one objective lens and one image sensor. By having at least two identical or similar arrangements of respectively one objective lens and one image sensor, the image capture device allows the capture of a stereo image which comprises an image provided for observation by the left eye and an image provided for observation by the right eye. The pivotability of the image capture device relative to the shaft component allows the viewing direction of the image capture device to be pivoted without toppling the horizon or tilting the stereo basis.

An endoscope comprises an endoscope apparatus as described here and an outer shaft.

BRIEF DESCRIPTION OF THE FIGURES

Embodiments are explained in more detail below on the basis of the attached figures. In detail.

DESCRIPTION OF THE EMBODIMENTS

Figure 1:
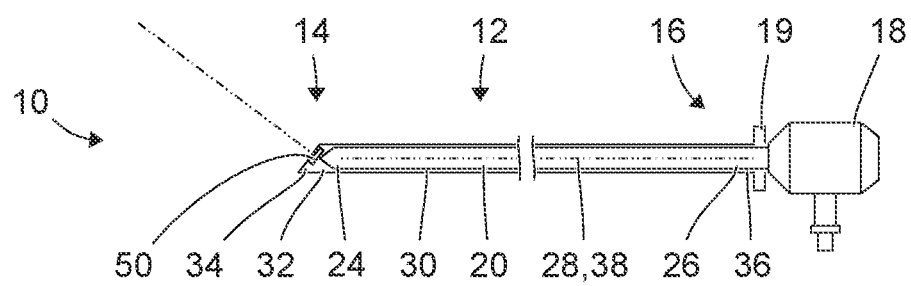
FIG. 1 shows a schematic illustration of an endoscope.

FIG. 1 shows a schematic illustration of an endoscope 10 with a shaft 12 which has a distal end 14 for insertion into a cavity and a proximal end 16. The proximal end 16 of the shaft 12 is adjoined by a proximal region 18, which is embodied as a handling device. As indicated in FIG. 1, the proximal region 18 can have one or more plug-in connectors for connecting the endoscope 10 to a light source and/or a power source, a camera control unit (CCU), and/or a monitor.

The shaft 12 of the endoscope 10 is formed by a shaft component 20 and an outer shaft 30. Both extend from the distal end 14 to the proximal end 16 of the shaft 12. The outer shaft 30 surrounds, in tubular fashion, a lumen 32, in which the shaft component 20 is arranged. The proximal end 26 of the shaft component 20 is mechanically rigidly connected to the proximal region 18 of the endoscope. The distal end 34 of the outer shaft 30 is sealed, in particular, by an optically transparent window component such that the lumen 32 of the outer shaft 30 is separated from the surroundings of the shaft 12 by the outer shaft 30, at least at and in the vicinity of the distal end 14 of the shaft 12. The proximal end 36 of the outer shaft 30 surrounds the proximal end 26 of the shaft component 20 and is mechanically rigidly connected to a rotary knob 19. The rotary knob 19 facilitates a manual rotation of the outer shaft 30 relative to the shaft component 20 and the proximal region 18 of the endoscope 10.

The distal end 24 of the shaft component 20 is mechanically connected to an image capture device 50 within the outer shaft 30, in such a way that the image capture device 50 does not rotate relative to the shaft component 20 about the longitudinal axis 28 of the shaft component 20 but can be pivoted within a predetermined solid angle range about two pivot axes that are orthogonal to the longitudinal axis 28 of the shaft component 20. As described below, the viewing direction of the image capture device 50 can be pivoted on a conical lateral face by rotation of the outer shaft 30 about its longitudinal axis 38.

Figure 2:
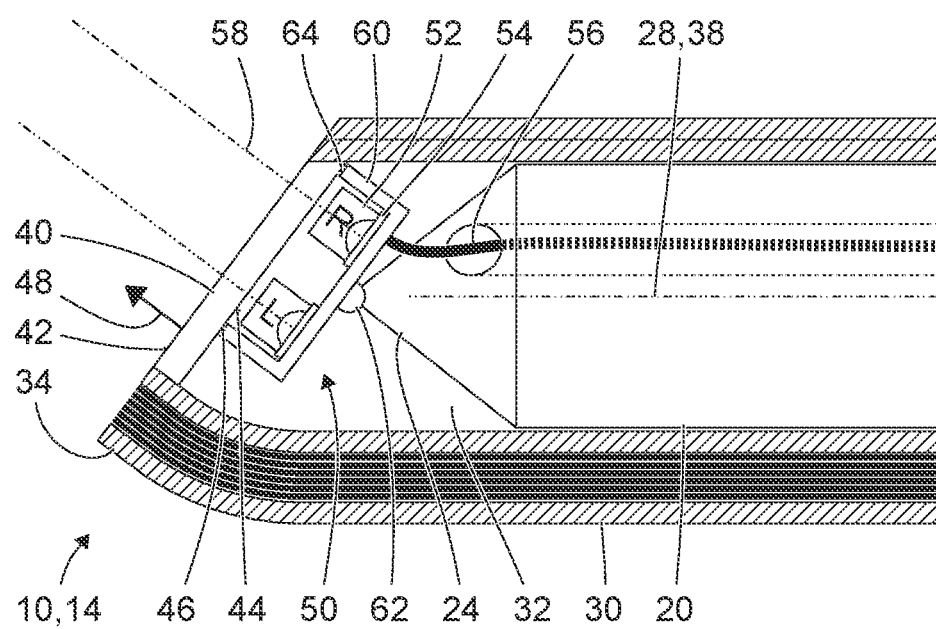
FIG. 2 shows a schematic magnified illustration of the distal end of the endoscope of FIG. 1.

FIG. 2 shows a magnified schematic illustration of the distal end 14 of the endoscope illustrated on the basis of FIG. 1. The plane of the drawing of FIG. 2 corresponds to the plane of the drawing of FIG. 1.

In FIG. 2, the outer shaft 30 is illustrated in section along a plane which contains the longitudinal axis 28 of the shaft component 20 and the longitudinal axis 38 of the lumen 32 of the outer shaft 30. What is indicated is that the outer shaft 30 is formed from two tubes arranged within one another in the illustrated example. Optical fibers for transmitting illumination light are arranged in an interstice with a sickle-shaped cross section between these two tubes.

The distal end of the outer shaft 30 is hermetically sealed by an optically transparent window component 40. The window component 40 has an outer, distal surface 42 as a light entry face and an inner, proximal surface 44 as a light exit face. In the illustrated example, the outer, distal surface 42 and the inner, proximal surface 44 of the window component 40 are each planar and are parallel to one another.

In the illustrated example, the image capture device 50 has two objective lenses 52, which each generate a real image, and two image sensors 54. Each image sensor 54 is assigned to one of the two objective lenses 52. Each image sensor 54 captures the real image generated by the assigned objective lens 52 and generates an image signal which represents the captured real image. The optical axes 58 of the objective lenses 52 are parallel to the viewing direction of the image capture device 50.

A signal line 56 connects the image capture device 50 to the proximal region 18 of the endoscope 10 (cf. FIG. 1). By way of the signal line 56, control signals and electric power can be transmitted to the image capture device 50 and the image signals generated by the image sensors 54 can be transmitted to the proximal region 18 of the endoscope 10.

The image capture device 50 comprises a carrier 60, to which the image sensors 54 and the objective lenses 52 are mechanically rigidly connected.

The carrier 60 is mechanically connected to the distal end 24 of the shaft component 20 by way of a joint 62. The joint 62—for example in the form of a gimbal joint—is embodied in such a way that the carrier 60, and hence the entire image capture device 50, can be pivoted relative to the shaft component 20 about two pivot axes that are orthogonal to the longitudinal axis 28 of the shaft component 20, but cannot be rotated about the longitudinal axis 28 of the shaft component 20.

In the illustrated example, the carrier 60 is embodied as a flat cup, the edge of which facing the window component 40 is embodied as a plane and annular sliding face 64. The sliding face 64 at the carrier 60 abuts against a sliding face 46 in an edge region of the inner, proximal surface 44 of the window component 40.

As a result of the sliding face 64 of the carrier 60 of the image capture device 50 abutting against the sliding face 46 in the edge region of the inner, proximal surface 44 of the window component 40 and on account of the symmetric configuration of the image capture device 50, the optical axes 58 of the image capture device 50 are parallel to the surface normal 48 of the surfaces 42, 44 of the window component 40 at all times. A rotation of the outer shaft 30 relative to the shaft component 20 about the longitudinal axis 38 of the lumen 32 of the outer shaft 30 brings about a rotation of the surface normals 48 of the surfaces 42, 44 of the window component on a conical lateral face, which is rotationally symmetric to the longitudinal axis 28, 38 of the shaft component 20 and of the outer shaft 30. This brings about a corresponding rotation of the optical axes 58 of the image capture device 50 on two conical lateral faces, the axes of symmetry of which are parallel to one another and to the longitudinal axis 38 of the lumen 32 of the outer shaft 30.

Figure 3:
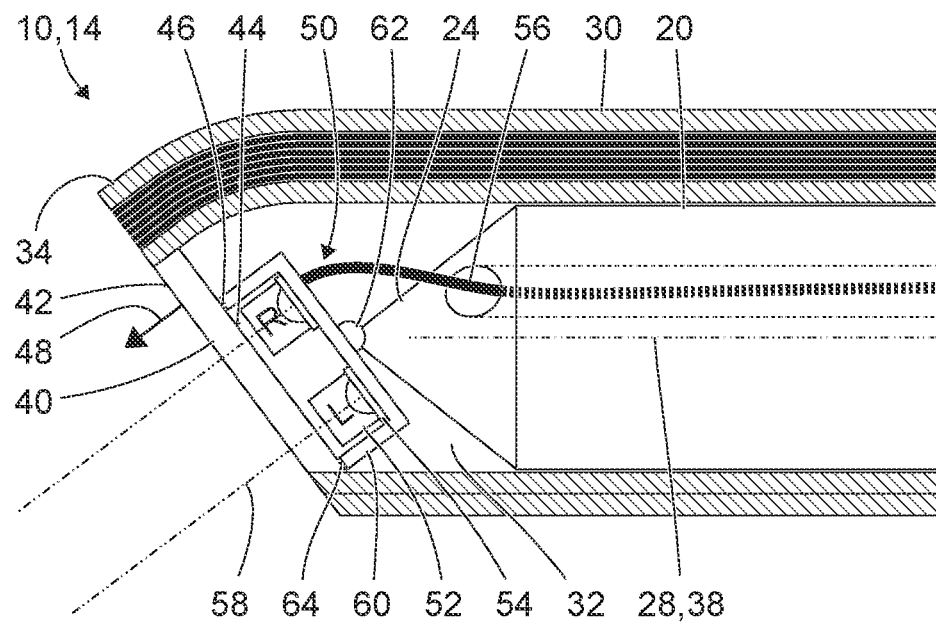
FIG. 3 shows a further schematic magnified illustration of the distal end of the endoscope of FIGS. 1 and 2.

FIG. 3 shows a further schematic illustration of the distal end 14 of the endoscope of FIGS. 1 and 2. The type of illustration in FIG. 3 corresponds to that of FIG. 2, in particular the orientation and relative position of the planes of the drawing and the section.

The configuration shown in FIG. 3 differs from the configuration shown in FIG. 2 in that the outer shaft 30 has been rotated relative to the shaft component 20 through 180° about the longitudinal axes 28, 38 of the shaft component 20 and of the outer shaft 30. Accordingly, the orientation of the surface normals 48 of the surfaces 42, 44 of the window component 40, the orientation of the optical axes 58, and the viewing direction of the image capture device 50 differ in the configuration shown in FIG. 3 from the configuration shown in FIG. 2.

In the case of the described rotation of the outer shaft 30 and hence of the optical axes 58 and the viewing direction 58 on conical lateral faces, as shown in FIGS. 2 and 3, the basis, i.e., the straight connecting line between the centers of the image sensors 54, is not rotated on account of the rotationally secured mechanical connection of the image capture device 50 to the distal end 24 of the shaft component 20. The unit made of objective lens 52 and image sensor 54 illustrated at the top in FIG. 3 is the unit made of objective lens 52 and image sensor 54, illustrated at the top in FIG. 3, for capturing an image provided for observation by the right eye and the unit made of objective lens 52 and image sensor 54 illustrated at the top in FIG. 3 is the unit made of objective lens 52 and image sensor 54, illustrated at the top in FIG. 3, for capturing an image provided for observation by the right eye. To make this clear, the objective lenses are labeled "R" and "L" in FIGS. 2 and 3. In the case of the rotation of the optical axes 58 and the viewing directions, the basis remains parallel to one and the same predetermined plane, which in turn is parallel to the longitudinal axis 28, 38 of the shaft component 20 and of the outer shaft 30 and parallel to the plane of the drawing of FIGS. 2 and 3.

Figure 4:
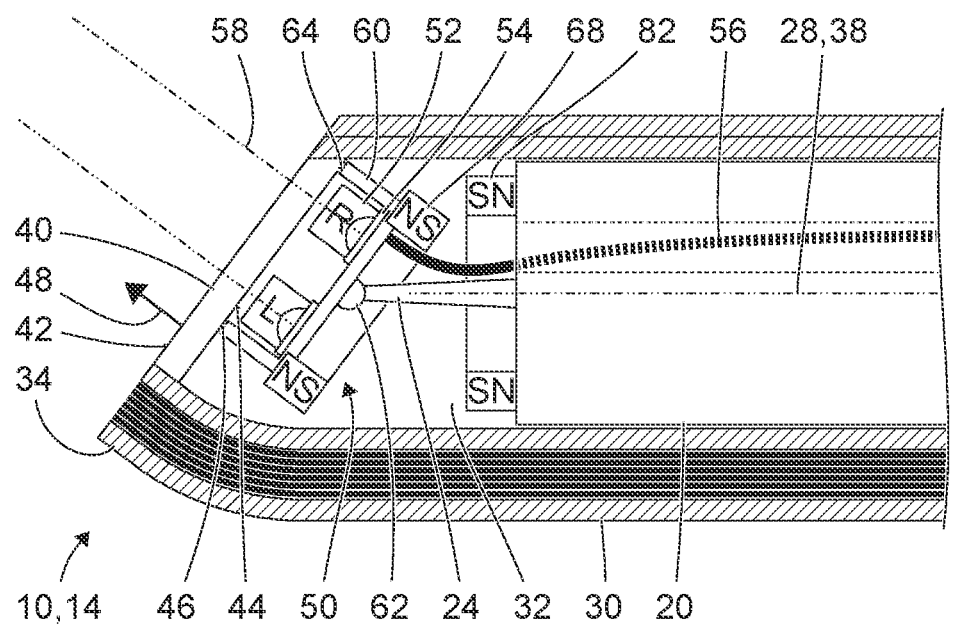
FIG. 4 shows a schematic illustration of a distal end of a further endoscope.

FIG. 4 shows a schematic illustration of a distal end 14 of a further endoscope which is similar to the endoscope illustrated on the basis of FIGS. 1 to 3 in terms of a few features, properties, and functions. The type of illustration in FIG. 4 corresponds to that of FIGS. 2 and 3. Described below are, in particular, features, properties, and functions, in terms of which the endoscope shown in FIG. 4 differs from the endoscope illustrated on the basis of FIGS. 1 to 3.

The endoscope shown in FIG. 4 has a magnet 68 at the carrier 60 of the image capture device 50 and a magnet 82 at the distal end 24 of the shaft component 20. In the illustrated example, the magnets 68, 82 at the image capture device 50 and at the distal end 24 of the shaft component 20 are each embodied in annular fashion. The magnets 68, 82 are oriented so as to repel one another.

The repulsive magnetic interaction between the magnets 68, 82 generates a distally oriented force on the image capture device 50, which presses the sliding face 64 of the carrier 60 against the sliding face 46 at the inner, proximal surface 44 of the window component 40. Together with an axial play of the image capture device 50 relative to the distal end 24 of the shaft component 20, this allows the image capture device 50 to abut against the window component 40 as intended at all times and hence have the envisaged orientation. In the illustrated example, this axial play is provided, for example, in the joint 62 between the carrier 60 of the image capture device 50 and the distal end 24 of the shaft component 20. Like in the case of the endoscope illustrated on the basis of FIGS. 1 to 3, the connection between the image capture device 50 and the distal end 24 of the shaft component 20 is rotationally secured such that pivoting of the viewing direction 58 on a conical lateral face is not accompanied by a rotation of the stereo basis.

Figure 5:
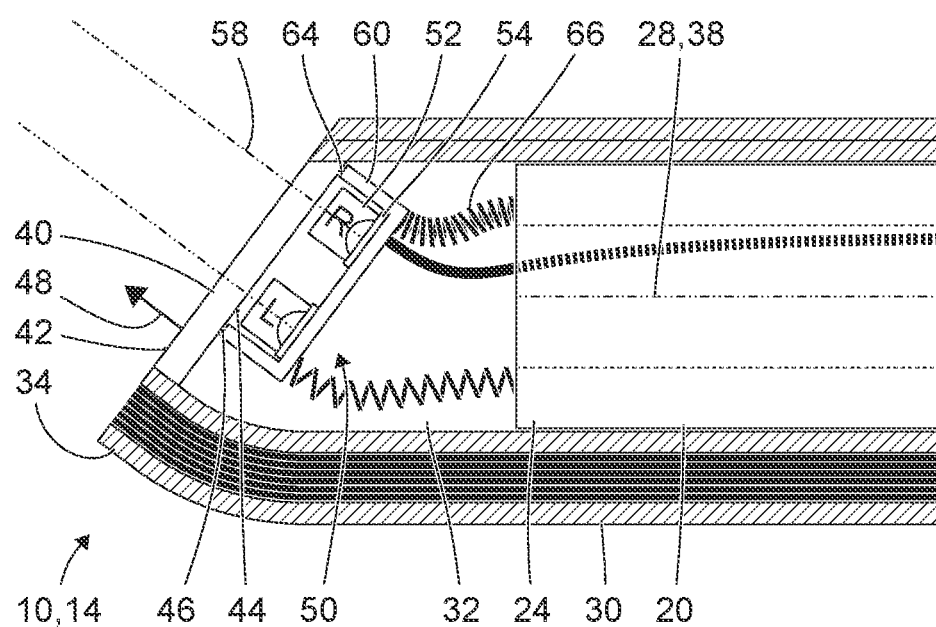
FIG. 5 shows a schematic illustration of a distal end of a further endoscope.

FIG. 5 shows a schematic illustration of a distal end 14 of a further endoscope which is similar to the endoscopes illustrated on the basis of FIGS. 1 to 4 in terms of a few features, properties, and functions. The type of illustration in FIG. 5 corresponds to the type of illustration in FIGS. 2 to 4. Described below are, in particular, features, properties, and functions of the endoscope shown in FIG. 5, in terms of which the latter differs from the endoscopes illustrated on the basis of FIGS. 1 to 4.

In the case of the endoscope shown in FIG. 5, a plurality of compression springs 66 are provided between the image capture device 50 and the distal end 24 of the shaft component 20. Two compression springs 66 are illustrated in FIG. 5. Three or more compression springs 66 which are arranged symmetrically in relation to the longitudinal axis 28 of the shaft component 20 are preferred. In the illustrated example, the compression springs 66 are embodied as helical springs.

The elastic restoring forces of the compression springs 66 press the sliding face 64 at the carrier 60 of the image capture device 50 against the sliding face 46 in the edge region of the inner, proximal surface 44 of the window component 40.

In the example illustrated in FIG. 5, no additional joint which connects the image capture device 50 in rotationally secured fashion to the distal end 24 of the shaft component 20 is provided. Instead, the flexural rigidity of the compression springs 66 prevents a rotation of the image capture device 50 relative to the distal end 24 of the shaft component 20. Alternatively, the springs 66 can be guided, for example, in drilled holes in the shaft component 20 such that each spring 66 is received almost entirely in the assigned drilled hole in the case of maximum compression and cannot bend to the side, or can only bend slightly to the side.

Figure 6:
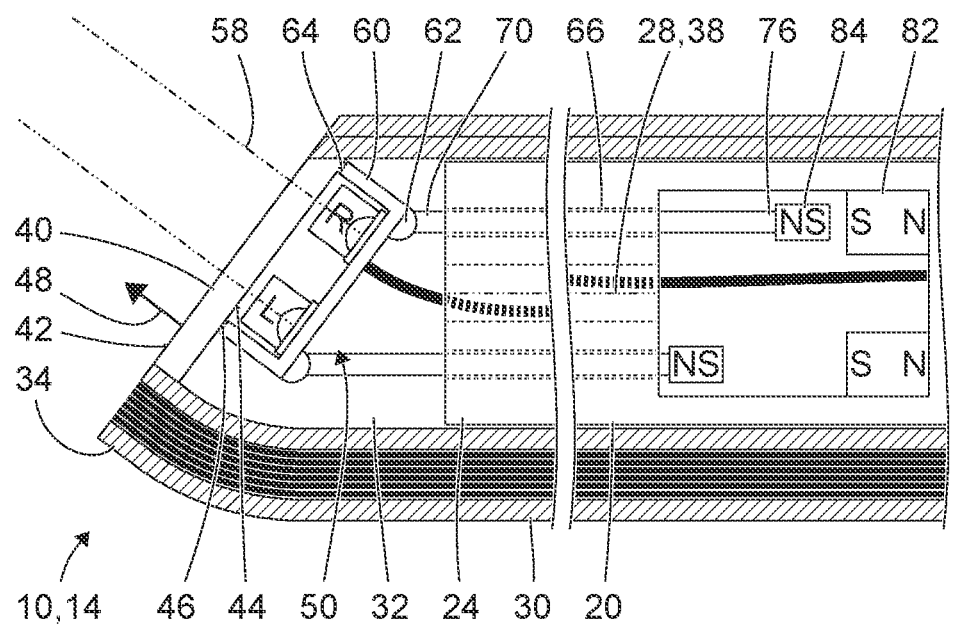
FIG. 6 shows a schematic illustration of a distal end of a further endoscope.

FIG. 6 shows a schematic illustration of a distal end 14 of a further endoscope which is similar to the endoscopes illustrated on the basis of FIGS. 1 to 5 in terms of a few features, properties, and functions. The type of illustration in FIG. 6 corresponds to the type of illustration in FIGS. 2 to 5. Described below are, in particular, features, properties, and functions of the endoscope shown in FIG. 6, in terms of which the latter differs from the endoscopes illustrated on the basis of FIGS. 1 to 5.

The endoscope shown in FIG. 6 has two rod-shaped force transmission devices 70, which extend within the shaft of the endoscope in a manner parallel to the longitudinal axis 28, 38 of the shaft component 20 and of the lumen 32 of the outer shaft 30. Each of the two force transmission devices 50 is guided at or, as indicated in FIG. 6, in the shaft component 20 with little play and friction but in a manner displaceable in its longitudinal direction. The distal end 74 of each force transmission device 70 is connected in mechanically articulated fashion to the carrier 60 of the image capture device 50 by way of a joint 72. The force transmission devices 70 are embodied with sufficient flexural rigidity to prevent a rotation of the image capture device 50 relative to the distal end 24 of the shaft component 20 about the longitudinal axis 28 of the shaft component 20.

A magnet 84 is arranged at the proximal end 76 of each force transmission device 70. Further, the endoscope has two magnets 82, which are oriented in such a way that they exert repulsive forces on the magnets 84 at the proximal ends 76 of the force transmission devices 70. By way of example, the magnets 82 are arranged close to the proximal end 26 of the shaft component, close to the proximal end 36 of the outer shaft 30 or in the proximal region 18 of the endoscope (cf. FIG. 1).

In the illustrated example, the magnets 82 are arranged in a cavity in the shaft component 20. Deviating from the illustration in FIG. 6, one or more magnets, which exert distally directed forces on the magnets 84 at the proximal ends 76 of the force transmission devices 70, can be rigidly connected to the outer shaft 30, for example as a ring-shaped arrangement at the inner side of the outer shaft 30.

The magnetic interaction between the magnet 82 and the magnets 84 at the proximal ends of the force transmission devices 70 generates distally directed forces on the force transmission devices 70, which are transmitted from the latter to the carrier 60 of the image capture device 50. The interaction between the magnets 82, 84 consequently presses the sliding face 64 at the carrier 60 of the image capture device 50 against the sliding face 46 in the edge region of the inner, proximal surface 44 of the window component 40. The magnets 82, 84 consequently ensure that the viewing direction of the image capture device 50 is parallel to the surface normal 48 of the surfaces 42, 44 of the window component 40 at all times. The configuration of the force transmission devices 70 with flexural rigidity ensures that the image capture device 50 does not rotate with the outer shaft 30 even in the case of a rotation of the outer shaft 30 relative to the shaft component 20 and despite friction between the sliding faces 46, 64.

Figure 7:
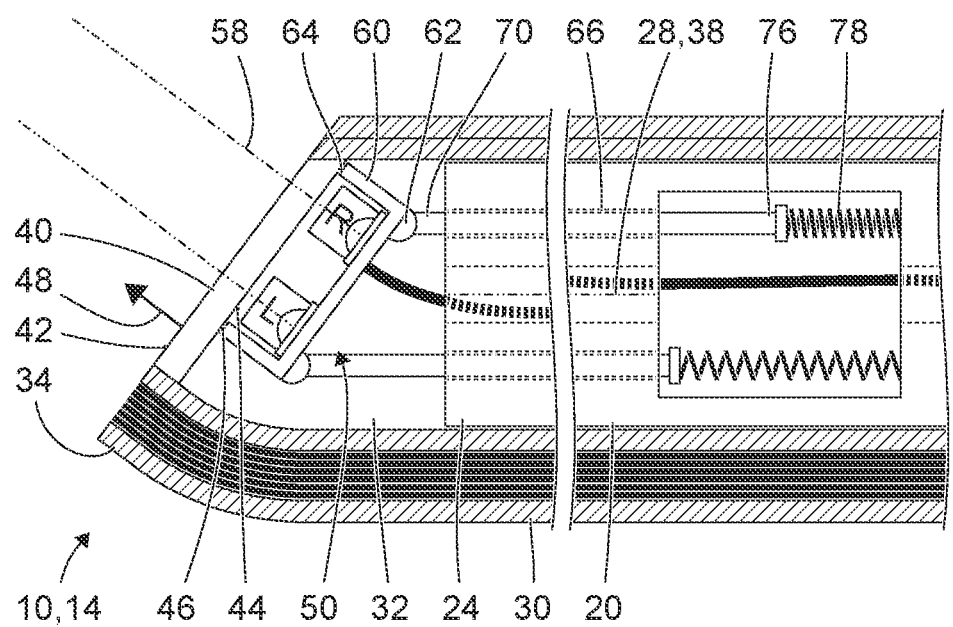
FIG. 7 shows a schematic illustration of a distal end of a further endoscope.

FIG. 7 shows a schematic illustration of a distal end 14 of a further endoscope which is similar to the endoscopes illustrated on the basis of FIGS. 1 to 5 and in particular to the endoscope illustrated on the basis of FIG. 6 in terms of a few features, properties, and functions. The type of illustration in FIG. 7 corresponds to the type of illustration in FIGS. 2 to 6. Described below are, in particular, features, properties, and functions of the endoscope shown in FIG. 7, in terms of which the latter differs from the endoscope illustrated on the basis of FIG. 6.

The endoscope shown in FIG. 7 differs from the endoscope illustrated on the basis of FIG. 6 in that, in particular, compression springs 78 are provided between the proximal ends 76 of the force transmission devices 70 and the shaft component 20. Elastic restoring forces of the springs 78 press the force transmission devices 70 in the distal direction and hence press the sliding face 64 at the carrier 60 of the image capture device 50 against the sliding face 46 in the edge region of the inner, proximal surface 44 of the window component 40.

In the example shown in FIG. 7, the compression springs 78 are arranged in a cavity in the shaft component 20. Deviating from the illustration in FIG. 7, the compression springs 78 can be arranged between the force transmission devices 70 and a component that is indirectly or directly mechanically rigidly connected to the shaft component 20, for example in the proximal region 18 of the endoscope 10 (cf. FIG. 1).

Figure 8:
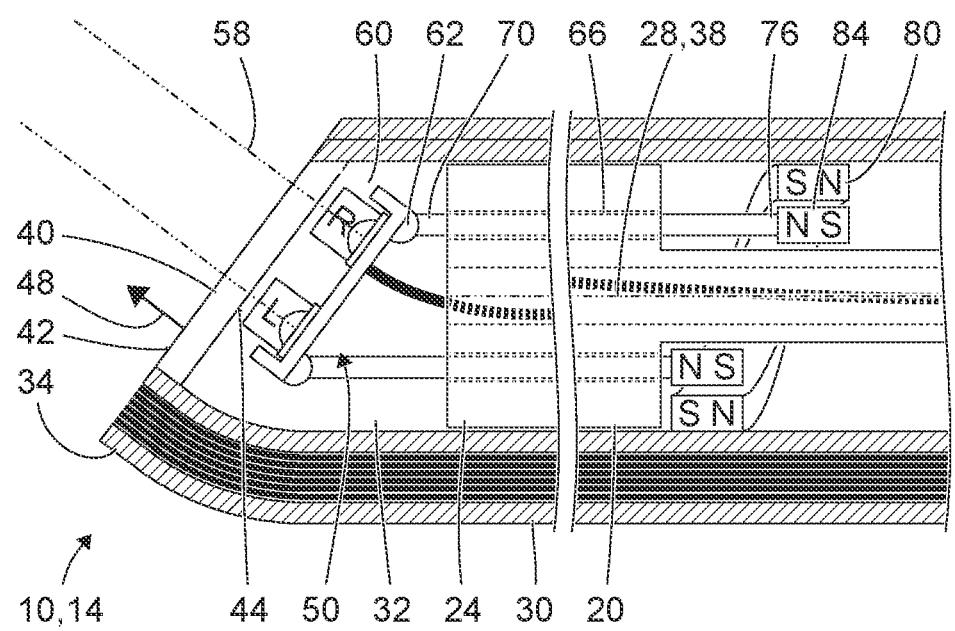
FIG. 8 shows a schematic illustration of a distal end of a further endoscope.

FIG. 8 shows a schematic illustration of a distal end 14 of a further endoscope which is similar to the endoscopes illustrated on the basis of FIGS. 1 to 5 and in particular to the endoscope illustrated on the basis of FIG. 6 in terms of a few features, properties, and functions. The type of illustration in FIG. 8 corresponds to the type of illustration in FIGS. 2 to 7. Described below are, in particular, features, properties, and functions of the endoscope shown in FIG. 8, in terms of which the latter differs from the endoscope illustrated on the basis of FIG. 6.

The endoscope shown in FIG. 8 differs from the endoscope shown in FIG. 6 in that, in particular, a ring-shaped circumferential magnet or a plurality of magnets 80 forming a ring-shaped circumferential arrangement is/are provided at the outer shaft 30. The magnet or magnets 80 does/do not lie in a plane orthogonal to the longitudinal axis 28, 38 of the shaft component 20 and of the lumen 32 of the outer shaft 30, but, for example, approximately in a plane that is tilted thereto and parallel to the surfaces 42, 44 of the window component 40.

The magnets 80 at the outer shaft 30 and the magnets 84 at the proximal ends 76 of the force transmission device 70 are oriented in such a way that they attract one another. The magnets 80 at the outer shaft 30 exert a force on each magnet 84 at the proximal end 76 of a force transmission device 70, the direction of which force depends on the position of the magnet 84 at the proximal end 76 of the force transmission device 70 and hence depends on the position of the force transmission device 70 itself. The magnets 80 at the outer shaft 30 consequently move each magnet 84 into a position that depends on the rotational position of the outer shaft 30, and hence of the magnets 80 at the outer shaft 30, relative to the shaft component 20. Since the distal ends 74 of the force transmission devices 70 are mechanically connected to the carrier 60 of the image capture device 50 by joints 72, the magnets 80 at the outer shaft 30 thus control the pivot position of the carrier 60 and hence of the entire image capture device 50. As a result of this, the carrier 60 does not have a sliding face in the endoscope shown in FIG. 8 and it is not in contact with the window component 40. Consequently, the magnets 80 at the outer shaft 30 control the pivot position of the image capture device 50 in contactless fashion.

The magnets 80 can be arranged at any location in the outer shaft 30, with the force transmission devices 70 having an appropriate length. In particular, the magnets 80 can be arranged in the rotary knob 19 at the proximal end 36 of the outer shaft 30, where more installation space is available.

It should be apparent that the foregoing relates only to the preferred embodiments of the present application and the resultant patent. Numerous changes and modification may be made herein by one of ordinary skill in the art without departing from the general spirit and scope of the invention as defined by the following claims and the equivalents thereof.

REFERENCE SIGNS

10 Endoscope
12 Shaft of the endoscope 10
14 Distal end of the shaft 12
16 Proximal end of the shaft 12
18 Proximal region of the endoscope 10
19 Rotary knob as operating element of the endoscope 10
20 Shaft component of the endoscope 10
22 Guiding device of the shaft component 20 for a force transmission device 70
24 Distal end of the shaft component 20
26 Proximal end of the shaft component 20
28 Longitudinal axis of the shaft component 20
30 Outer shaft of the endoscope 10
32 Lumen of the outer shaft 30

34 Distal end of the outer shaft 30
36 Proximal end of the outer shaft 30
38 Longitudinal axis of the outer shaft 30
40 Window component at the distal end 34 of the outer shaft 30
42 Outer, distal surface of the window component 40
44 Inner, proximal surface of the window component 40
46 Sliding face in an edge region of the inner, proximal surface 44 of the window component 40
48 Surface normal of the surfaces 42, 44 of the window component 40
50 Image capture device of the endoscope 10
52 Objective lens of the image capture device 50, for generating a real image
54 Image sensor of the image capture device 50, for capturing the real image generated by the objective lens 52 and for generating an image signal
56 Signal line for transmitting power and/or a control signal to the image sensor 54 and/or for transmitting the image signal from the image sensor 54
58 Optical axis of the objective lens 52 of the image capture device 50
60 Carrier of the image capture devices 50
62 Joint between the image capture device 50 and the distal end 24 of the shaft component 20
64 Sliding face at the carrier/housing
66 Compression spring between the image capture device 50 and the distal end 24 of the shaft component 20
68 Magnet at the image capture device 50
70 Force transmission device in or at the shaft component 20
72 Joint between the image capture device 50 and the distal end 74 of the force transmission device 70
74 Distal end of the force transmission device 70
76 Proximal end of the force transmission device 70
78 Spring at the proximal end of the force transmission device 70
80 Magnet at the outer shaft 30 of the endoscope 10
82 Magnet at the shaft component 20 or at a proximal region 18 of the endoscope 10
84 Magnet at the proximal end of the force transmission device 70

The invention claimed is:

1. An endoscope apparatus comprising:
a shaft component having a proximal end and a distal end for insertion into a cavity, wherein the shaft component is arranged in an outer shaft or provided and embodied for arrangement in the outer shaft;
an image capture device having an objective lens for generating a real image and an image sensor for capturing the real image and for generating an image signal which represents the captured real image, wherein the image capture device is arranged at the distal end of the shaft component;
a pivot joint device which couples the image capture device to the shaft component in a manner pivotable about two orthogonal axes but rigid in respect of a rotation about a longitudinal axis of the shaft component;
a pivot control device for setting a pivot position of the image capture device guided by rotational movement of the outer shaft relative to the image capture device and the shaft component.

2. The endoscope apparatus as claimed in claim 1, wherein the pivot control device comprises:
a first sliding face in the outer shaft,
a second sliding face mechanically rigidly connected to the image capture device, for abutment against the first sliding face in the outer shaft.

3. The endoscope apparatus as claimed in claim 2, wherein the first sliding face is arranged at an edge of an inner surface of a window component of the outer shaft.

4. The endoscope apparatus as claimed in claim 3, wherein:
a surface normal of the inner surface of the window component is tilted relative to a longitudinal axis of a distal end of the outer shaft, and
the first sliding face is a portion of the inner surface of the window component.

5. The endoscope apparatus as claimed in claim 2, wherein the second sliding face is provided at a frame or a carrier or a housing of the image capture device.

6. The endoscope apparatus as claimed in claim 2, wherein the objective lens of the image capture device is arranged between two portions of the second sliding face.

7. The endoscope apparatus as claimed in claim 1, further comprising:
a first magnet which is mechanically rigidly connected or mechanically coupled to the image capture device by way of a force transmission device;
a second magnet which is mechanically rigidly connected to the shaft component or to a proximal region of the endoscope apparatus or to the outer shaft;
wherein the first magnet and the second magnet are arranged and oriented in such a way that a force generated by a magnetic field between the first magnet and the second magnet exerts a distally directed force on the image capture device.

8. The endoscope apparatus as claimed in claim 7, comprising:
a plurality of first magnets which are mechanically rigidly connected or mechanically coupled to the image capture device by way of force transmission devices,
wherein the first magnets and the second magnet are arranged and oriented in such a way that a force generated by a magnetic field between the first magnets and the second magnet exerts a distally directed force on the image capture device.

9. The endoscope apparatus as claimed in claim 7, comprising:
a plurality of second magnets which are mechanically rigidly connected to the shaft component or to a proximal region of the endoscope or to the outer shaft;
wherein the first magnet or the first magnets and the second magnets are arranged and oriented in such a way that forces generated by magnetic fields between the first magnet or magnets and the second magnets exert distally directed forces on the image capture device.

10. The endoscope apparatus as claimed in claim 1, further comprising:
a spring or another elastic device with a first end, which is directly mechanically connected or mechanically coupled to the image capture device by way of a force transmission device, and a second end, which is directly or indirectly mechanically connected to the shaft component or a proximal region of the endoscope apparatus,
wherein the spring or other elastic device exerts a distally directed force on the image capture device.

11. The endoscope apparatus as claimed in claim 10, comprising:

a plurality of springs or other elastic devices each with a first end, which is directly mechanically connected or mechanically coupled to the image capture device by way of the force transmission device, and each with a second end, which is directly or indirectly mechanically connected to the shaft component or the proximal region of the endoscope, wherein the springs or other elastic devices exert distally directed forces on the image capture device.

12. The endoscope apparatus as claimed in claim 1, further comprising:

a plurality of first magnets which are mechanically rigidly connected or mechanically coupled to the image capture device by way of respective force transmission devices;

a magnet arrangement of one or more second magnets which is mechanically rigidly connected to the outer shaft, for generating a guiding magnetic field which generates a force on each of the first magnets in a direction of a position that depends on the rotational position of the image capture device and the shaft component relative to the outer shaft.

13. The endoscope apparatus as claimed in claim 7, wherein each of a plurality of force transmission devices comprises a rod-like component which is guided so as to be movable in its longitudinal direction in or at the shaft component.

14. The endoscope apparatus as claimed in claim 13, wherein:

the pivot joint device comprises a plurality of joints, each of the plurality of joints connects the image capture device to a distal end of one of the rod-like components.

15. The endoscope apparatus as claimed in claim 1, wherein:

the endoscope apparatus is a stereo endoscope apparatus, the image capture device comprises two identical or similar arrangements of respectively one objective lens and one image sensor, which are mechanically rigidly connected to one another.

\* \* \* \* \*